United States Patent [19]

Orth et al.

[11] 3,959,080

[45] May 25, 1976

[54] CARRIER MATRIX FOR THE FIXATION OF BIOCHEMICALLY EFFECTIVE SUBSTANCES AND PROCESS FOR THE PREPARATION THEREOF

[75] Inventors: Hans Dieter Orth; Wolfgang Brummer; Michael Klockow; Norbert Hennrich, all of Darmstadt, Germany

[73] Assignee: Merck Patent Gesellschaft mit beschrankter Haftung, Darmstadt, Germany

[22] Filed: Sept. 26, 1973

[21] Appl. No.: 400,898

[30] Foreign Application Priority Data
Sept. 26, 1972 Germany............................ 2247163

[52] U.S. Cl.................................. 195/63; 195/68; 195/DIG. 11; 260/15; 260/112 R; 260/231 CM; 260/232
[51] Int. Cl.²...................... C07G 7/02; C07G 17/00
[58] Field of Search................ 195/63, 68, DIG. 11; 260/15, 112 R, 231 CM, 232

[56] References Cited
UNITED STATES PATENTS

| | | | |
|---|---|---|---|
| 3,654,083 | 4/1972 | Moelker............................... | 195/63 |
| 3,666,733 | 5/1972 | Epton................................... | 195/63 |
| 3,741,871 | 6/1973 | Weeks.................................. | 195/63 |
| 3,746,622 | 7/1973 | Nishikawa.......................... | 195/66 R |
| 3,775,253 | 11/1973 | Dieter................................... | 195/63 |
| 3,914,183 | 10/1975 | Johansson............................ | 195/63 |

*Primary Examiner*—Donald E. Czaja
*Assistant Examiner*—Edward Woodberry
*Attorney, Agent, or Firm*—Millen, Raptes & White

[57] ABSTRACT

Biochemically active compounds e.g., proteins and particulate biological materials such as bacteria and viruses, are immobilized on a water-swellable or water-insoluble matrix by covalent bonding to a partially crosslinked polymer containing reactive groups capable of binding the biochemically active compound thereto.

26 Claims, No Drawings

CARRIER MATRIX FOR THE FIXATION OF BIOCHEMICALLY EFFECTIVE SUBSTANCES AND PROCESS FOR THE PREPARATION THEREOF

This invention relates to a carrier matrix for the immobilization of biochemically active substances, particularly polypeptides and proteins, e.g., enzymes, and to processes for the preparation and use of this matrix.

Matrix-bound biologically active substances are known, e.g., see "*Angewandte Chemie*" (Applied Chemistry), 84: 319–330 (1972) and *Scientific American*, March, 1971, pages 26 ff. In being affixed to the matrix, biochemically active substances normally react at amino groups thereof, also at OH— or SH— groups thereof, or at aromatic, e.g., phenyl nuclei contained in these substances, in each case with the formation of new covalent linkages to the carrier matrix. Suitable matrix substances heretofore used include, for example, polysaccharides and various derivatives thereof, e.g., carboxymethylcellulose (CMC), cellulose, and especially agarose, and certain vinyl polymers, e.g., copolymers of ethylene and maleic anhydride. These carriers are used as such and in a partially crosslinked form; in some cases they are activated by introducing reactive groups for covalent linking of biologically active substances thereto. Agarose has proved to be an especially advantageous carrier substance, since it possesses such a high initial porosity that it is still usable as a matrix for enzymes in spite of partial shrinkage during activation, e.g., with BrCN. A main disadvantage of agarose is its high price, which makes the utilization of agarose-bound enzymes economically unfeasible for industrial scale enzymatic conversions, e.g., amylose saccharification, invert sugar production, etc. Therefore, it would be desirable to have available a less expensive carrier matrix having the above-indicated valuable properties of cross-linked agarose.

OBJECTS OF THE INVENTION

Accordingly, it is a general object of this invention to provide improved carrier matrices capable of immobilizing biochemically active compounds by covalent bonding thereto without loss of biochemical activity.

Another object of this invention is to provide biochemically active compounds immobilized by covalent bonding to a water insoluble carrier material.

A further object of the invention is to provide biochemically active compounds covalently bonded to a carrier material in such a way that steric hindrance by the carrier is greatly reduced or eliminated.

An additional object of the invention is to provide the above preparations wherein covalent binding between the carrier and one or more biochemically active compounds is selectively effected via different functional groups.

A similar object of the invention is to provide processes for the preparation and use of the above preparations.

Other objects of the invention will become apparent to those skilled in the art upon further study of the specification and appended claims.

SUMMARY OF THE INVENTION

Briefly, the above and other objects are attained in one aspect of the present invention by providing a process for preparing a water swellable or water insoluble polymeric material capable of covalently bonding biochemically active compounds thereto, which comprises: (a) reacting an uncross-linked water soluble or water swellable polymer containing crosslinkable acid hydrazide or acid azide groups with a bifunctional crosslinking agent reactive with said groups to covalently crosslink a portion of said groups, and (b) activating at least a portion of the residual uncrosslinked acid hydrazide or acid azide groups of the resultant crosslinked polymeric material into reactive groups capable of covalent bonding to an amino, hydroxyl, mercapto or phenyl group of a biochemically active compound by at least one further reaction selected from the group consisting of (i) reacting said residual groups with nitrous acid and (ii) unilaterally substituting said residual groups with a bifunctional agent having a first functional group reactive with said residual groups and a second unreacted functional group capable of said covalent bonding.

DETAILED DISCUSSION OF THE INVENTION

According to the present invention, it is now possible to introduce not only a single reactive group, but selectively different reactive groups into a biochemical immobilizing matrix. Thus, the covalent linkages between the matrix and one or more chemically active substances can be effected via different (basic, acidic, aromatic) functional groups; for example, the optimal immobilization reaction conditions which are different for each individual substance can thus be more readily fulfilled in order to extensively maintain the activity of the active substance. The advantages of such properties will be readily apparent to those skilled in the art. Furthermore, the binding of the biochemically active substance need not be accomplished in all cases directly on the surface of the matrix, as it is also possible to interpose a side chain spacer. Thereby the spatial orientation, e.g., of the active center of an enzyme with respect to its substrate or effector, is greatly facilitated, especially if this spacer substance is likewise of a high molecular weight, e.g., on the order of 20000 or higher. If this possibility is not provided, the activity of a biochemically active material, e.g., a bound enzyme, cannot always be fully exploited in immobilized form due to steric hindrance by the carrier.

It has now been found that is possible to employ certain inexpensive, water-soluble polymers as starting materials for preparing enzyme matrices which surprisingly have these desired properties. These materials are water-soluble polymers containing organic acid hydrazide groups or organic acid azide groups, preferably carboxylic acid hydrazide or azide groups. These commercially available starting materials are first partially crosslinked by reacting the acid hydrazide or azide groups with a bifunctional crosslinking reagent. Any remaining, uncrosslinked functional groups, especially acid hydrazide groups, are then at least partially converted into the required groups appropriate for activation by covalent coupling with the biochemically active substances.

Biochemically active substances useful in the present invention include but are not limited to biological materials such as enzymes, hormones, antigens, antibodies and other plasma proteins, blood group substances, and biochemically active derivatives of all these materials; furthermore enzyme effectors, i.e., enzyme substrates, enzyme inhibitors, enzyme activators, enzyme stabilizers, allosteric effectors, antibodies, coenzymes, and biochemically active derivatives of all these materials.

Moreover, it is also possible to affix particulate natural substances, e.g., viruses and bacteria, if they contain the appropriate groups capable of reaction with the reactive groups of the polymer, e.g., amino, OH—, SH—, phenyl etc.

According to the present invention, a water-soluble polymer of sufficiently high molecular weight so as to be capable of crosslinking to a water insoluble polymer is employed. A polymer containing e.g. hydrazide or acid azide groups is partially crosslinked by reaction of these groups with a bifunctional crosslinking reagent, and any residual acid hydrazide or acid azide present uncrosslinked in the thus-obtained product is simultaneously or subsequently converted at least partially into further different reactive groups which can covalently bind with the biochemically active substances.

The polymers used are preferably water-soluble hydrazides of CMC or of polyacrylic acid and the copolymers thereof (e.g., with 70 mol % acrylamide). The use of CMC as an enzyme carrier is known from the literature, e.g., from *Angewandte Chemie* 84: 319–330 (1972), l.c., and the literature cited therein. Normally, CMC is converted from the carboxyl form via the methyl ester and the corresponding hydrazide into the reactive azide configuration. However, not entirely satisfactory results have been obtained in this procedure so far. With the use of a low-substituted CMC which is not water-soluble (0.5 – 0.8 meq./g.) customarily employed as an ion exchanger for the chromatographic purification of many enzymes, only small amounts of protein are bound after activation (10 – 20 mg/g of matrix), and these have low residual activities (<50%). On the other hand, when using water-soluble, highly substituted CMC (2 – 4.5 meq/g) as the starting material for immobilizing proteins in a weakly alkaline aqueous medium, entirely or partially soluble products are obtained. During this process, a portion of the azide groups is hydrolyzed to water-soluble COOH—groups, and thus part of the protein-CMC conjugate becomes water-soluble and is lost. In the remaining insoluble proportion, the protein is strongly crosslinked and thereby sterically hindered to a large extent.

According to this invention, the starting material is preferably a water-soluble, highly substituted CMC hydrazide containing about 2 – 4.5, preferably 3 – 3.5 meq. of acid hydrazide groups per gram of dry CMC. The average degree of substitution, i.e., the average number of acid hydrazide groups present on one glucose unit, ranges between about 0.65 and 1.0. The average degree of polymerization is approximately 150 – 2000, preferably about 1500 glucose units per CMC molecule.

Just as the aforementioned CMC hydrazides, it is also possible to employ uncrosslinked, water-soluble hydrazides of polymeric acrylic acid, preferably as a random, block or graft copolymer with acrylamide. In this connection, the mole ratio of acrylic acid hydrazide: acrylic acid amide can be about 1 : 1 to 1 : 40, preferably of 1 : 1 to 1 : 5. The content of acid hydrazide groups in these copolymers then ranges from about 6.3 to 0.34 meq/g. Suitable polyacrylic acid homopolymers and copolymers have a molecular weight of about 5,000 – 200,000, preferably about 10,000 – 30,000.

The partial crosslinking process is preferably accomplished with a bifunctional crosslinking reagent of the general Formula I:

$$X_1-Y-X_2 \quad I$$

wherein $X_1$ and $X_2$ are each independently —CHO, —CH$_2$Hal,

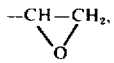

—NH$_2$, —COHal, —NCO, or —SCN; Hal is Cl, Br, or I, and Y is a single covalent bond or an alkylene hydrocarbon chain of up to 18 carbon atoms, optionally interrupted by up to 4 oxygen atoms.

The groups $X_1$ and $X_2$ are preferably alike; however, they can also be different from each other. Y is preferably an unbranched saturated divalent alkylene chain of the formula —C$_n$H$_{2n}$— (n = 1–18, preferably 1–8, especially 3–6). Suitable crosslinking agents include but are not limited to dialdehydes, dicarboxylic acid halides, diepoxides, diamines, diisocyanates and dirhodanides; halocarboxylic acid halides, e.g., chloroacetyl chloride, bromoacetyl chloride, or iodoacetyl chloride; halogenated epoxides, e.g., epichlorohydrin or epibromohydrin; and halides of aldehydic acids, e.g., glutaraldehydic acid chloride. Expecially preferred crosslinking agents are glutaric dialdehyde and hexamethylenediamine.

By the crosslinking reaction, respectively two strands of the polymer are linked together by groups corresponding to the general formula —CO—NH—Z—Y—Z'—NH—CO— wherein Y has the above-indicated values and Z and Z' are each independently a single covalent bond, —N=CH—, —NHCH$_2$—, —NHCH$_2$CHOH—, —NHCO—, —NH—CO—NH—, or —NH—CS—NH—, preferably wherein the two groups Z and Z' are alike.

The partial crosslinking of the polymeric acid hydrazide is normally effected in an aqueous solution and at appropriate pH values dependent on the crosslinking reagent. For example, the reaction with dialdehydes is advantageously conducted in a slightly acidic solution (pH about 4.5). The reaction temperatures are approximately 0° to 50°C., preferably 15° to 30°C. At least 10 molar percent crosslinking of the hydrazide groups is generally required; for complete conversion into a water-insoluble, highly swelled gel, crosslinking 15–20 molar percent of the hydrazide groups present is generally sufficient, and preferably at least 70 – 80 % of the hydrazide groups are uncrosslinked. The swelling capacity and/or porosity of the thus-obtained gel can be controlled by varying the crosslinking reaction conditions, e.g., the concentration of the given water-soluble polymer and the pH at which the crosslinking reaction is accomplished. In this manner, the swelling capacity of the gel, measured as water absorption per gram of dry gel substance, can be varied from 10 to 80 ml H$_2$O/g. Such a voluminous gel structure is, for steric reasons, of special advantage for the full development of the activity of a biochemically active substance bound by a covalent linkage to such a matrix.

Complete crosslinking of all hydrazide groups cannot be achieved even by the use of an excess of crosslinking reagent, and is furthermore undesirable; the thus-obtained crosslinked product still contains either acid hydrazide groups or other reactive groups formed from the acid hydrazide groups with the bifunctional reagent by "unilateral" reaction, e.g., wherein one function of the bifunctional reagent is as yet unreacted. The reaction of the water-insoluble polymer with additional bifunctional reagent leads predominantly to "unilateral" substitution, which is believed to be due to an interface reaction.

Any uncrosslinked functional groups, especially acid hydrazide groups, still present in the thus-obtained product can be converted, according to this invention, at least partially into other reactive groups capable of reacting with the biochemically effective substances by activation.

A preferred form of activation is the conversion of the hydrazide groups into azide groups with nitrous acid, suitably with sodium nitrite in 0.01N hydrochloric acid at low temperatures of between about −10° and +10°C.

The residual acid hydrazide groups can also be activated by reaction with a bifunctional reagent of the above-mentioned Formula I. As indicated above, only one of the reactive groups $X_1$ and $X_2$ reacts with the acid hydrazide groups, whereas the other reactive groups is preserved and available to react with a biochemically active substance, e.g., with the amino group of an enzyme. Thus, for example, with dialdehydes, the monoacylhydrazones are obtained, the free aldehyde groups of which can be reacted with the amino groups of enzymes. If desired, the C=N bonds of the thus-produced Schiff bases can be reduced to CH—NH— bonds, e.g., with $NaBH_4$. The reaction with the bifunctional reagents of Formula I is suitably accomplished under the above-indicated conditions.

The activation can also take place with bifunctional reagents which are only poorly suitable for crosslinking. For example, it is possible to react acid hydrazides with nitrobenzaldehydes, e.g., p-nitrobenzaldehyde, thus producing the corresponding acylhydrazones of the nitrobenzaldehydes. The nitro groups can then be reduced to amino groups; the latter can be diazotized and coupled with aromatic groups present in the biochemically active substances, e.g., with the tyrosine portion of albuminous or other proteinaceous substances.

If it is desired to interpose a side chain spacer, the partially crosslinked polymeric acid hydrazides and/or azides cal also be reacted successively with several reagents. In this process, the length of the interposed side chains can be varied arbitrarily dependent on the type of spacer reagent employed and on the number of successive chain-extending reactions.

For example, azides can be converted into the corresponding N-(aminoalkyl)-amides with an excess of diamines, e.g., hexamethylenediamine; the free amino groups of these products are then converted with dialdehydes, e.g., glutaric dialdehyde, or with nitrobenzaldehydes, e.g., p-nitrobenzaldehyde, to the corresponding Schiff bases in the manner described herein. Substances obtained in this way have, for example, the following schematic partial formulae:

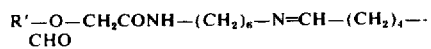

or

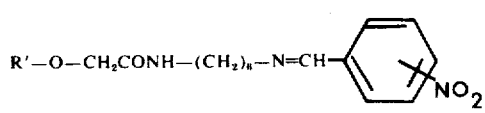

wherein R' is a partially crosslinked strand of the polymer, e.g., a cellulose chain or the chain of a vinyl polymer. The thus-produced compounds can then either be reacted directly with the biochemically active substances via the terminal-positioned functional group, e.g., the aldehyde group, or the terminal-positioned functional group can first be further converted as disclosed above, e.g., by reduction or diazotization, and can then be coupled with the biochemically active substance.

It is also possible to effect the partial crosslinking and activation processes simultaneously. For this purpose, the polymeric acid hydrazide is reacted under the above-indicated conditions with a two to five-fold excess of the bifunctional reagent. Preferred difunctional reagents here again are the dialdehydes, especially glutaric dialdehyde.

The crosslinked and activated carrier matrix is normally reacted with the compounds affixed thereto in an inert polar solvent, preferably water, at pH values of between 4 and 14. In the fixation of enzymes, the process is advantageously conducted in a buffered aqueous solution, using any inert buffer suitable for maintaining a pH within the desired range. For example, a pH of 4 to 5 can be buffered with 0.005 – 0.5 M, preferably 0.05 M acetate buffer, while a pH range of 5 to 8 can be maintained with a phosphate buffer of the same concentration. In the pH range of 7 to 9, suitable buffers are triethanolamine, tris(hydroxymethyl)aminomethane, or boric acid/borax buffers of the same concentration, and in the pH range of 9 to 11, a carbonate/bicarbonate buffer. Also other buffers effective in the indicated pH ranges can be utilized, as the nature of the buffer is not critical so long as it is inert and within the pH range desired. Many such buffer systems can be found in the literature. The temperatures are of course below deactivation temperatures of the particular enzymes employed, preferably at about 0° to 25°C.

The quantitative ratio of activated carrier matrix to the compound to be fixed is about 5:1 to 1:5, preferably about 2:1. For compounds having a molecular weight over about 3000, this ratio can be calculated in parts by weight, based on the dry weight. In contrast thereto, in the fixation of compounds having a molecular weight below about 3000, these values refer to the number of moles (or millimoles) or reactive groups in the respective reactants.

For purposes of fixation, the compound containing reactive groups can be provided in the buffered aqueous solution and the carrier matrix can be stirred into this solution; it is also possible to stir the compound to be affixed, preferably in an aqueous buffered solution, into the carrier suspension. Optionally, the reaction mixture furthermore contains conventional stabilizers, e.g., suitable protein stabilizers include but are not limited to SH-reagents such as cysteine or mercaptoethanol, and/or $Ca^{++}$ ions. Subsequently, the reaction mixture is maintained for a reaction time of from about 5 minutes to about 48 hours, normally about 1 hour, at a pH of between 4 and 14, in case of most proteolytic enzymes preferably at a pH of about 9. Optional coupling pH's for a given system are readily determined by simple experimentation. Thereafter, the reaction product is isolated from the suspension in a conventional manner. Normally, the insoluble product is filtered off and washed in the usual way in order to remove the absorbed but uncoupled remainder of the biochemically active compound. In the case of enzymes, salt solutions known for this purpose are preferably used, with a molarity of up to about 3 and a pH value of between 4 and 14, as appropriate for the particular enzyme. Suitable salts are particularly readily soluble and strongly dissociating alkali metal salts, e.g., NaCl or $Na_2SO_4$. However, it is also possible to utilize buffer solutions, optionally in a mixture with these alkali metal salt solutions. In many cases, it is also advantageous to conduct the fixation in the presence of alkaline Lewis base catalysts, especially pyridine.

Among the biologically active compounds to be affixed to the matrix, suitable proteins include but are not limited to the following enzymes:

Proteases and peptidases, e.g., trypsin, chymotrypsin, pepsin; papain, ficin, bromelin, bacterial proteinases (thermolysin, subtilisin), fungal proteinases, aminopeptidase and carboxypeptidase; enzymes of the nucleic acid metabolism, e.g., endonucleases (deoxyribonucleases, ribonucleases) or exonucleases (phosphodiesterases I and II; DNA-polymerase, RNA-polymerase); other hydrolases, e.g., $\alpha$-amylase, $\beta$-amylase, amyloglucosidase, saccharase (=invertase), lactase (= $\beta$-galactosidase), $\beta$-glucuronidase, penicillinase, urease, acidic phosphatase, alkaline phosphatase; transferases, e.g., glycerate kinase, glutamate-pyruvate transaminase, glutamate-oxalacetate transaminase; oxidoreductases, e.g., lactate dehydrogenase, malate dehydrogenase, steroid dehydrogenases, steroid hydroxylases, glucose dehydrogenase, glucose oxidase, L- and D-amino acid oxidase, phenol oxidase, catalase, peroxidase, uricase; lyases, e.g., amino acid decarboxylases and ketocarboxylic acid decarboxylases; carboxyl esterases and deacylases; isomerases, e.g., glucose isomerase; synthetases, e.g., amino acid tRNA ligases, peptide synthetases and carboxylases.

Suitable enzyme effectors include but are not limited to coenzymes, e.g., NAD(P), NAD(P)H, pyridoxamine phosphate, pyridoxal phosphate, thiamine pyrophosphate, coenzyme A and biotin. Furthermore useful are flavins, folic acid and the derivatives thereof, amino acids, nucleosides and nucleotides, steroids and enzyme inhibitors. These latter can be either of natural origin, e.g., protease inhibitors from animal or vegetable matter, or of synthetic origin, e.g., mercapto compounds, benzamidines and m-amino-phenylboronic acid.

The enzyme contents of conjugates containing enzymes fixed in accordance with this invention are high. For example, enzyme contents of up to 20% and higher are easily attained, as determined by micro-determination of the nitrogen content. Also the activities of these fixed enzymes are excellent, typically 70–100% based on the activity of the enzyme prior to immobilization.

The activities of the enzymes fixed in accordance with the present invention can be conventionally determined in the same way as the activities of the native enzymes themselves. For the immobilized trypsin, BAEE (N-benzoyl-L-arginine ethyl ester) can be used as the substrate. The reaction speed is measured by continuous titration, e.g., with NaOH, of the carboxyl groups liberated from the substrate, at a constant pH. The pH value selected is that which is optimal for the enzyme activity being investigated. The reaction temperatures are normally about 20°–55°C, preferably about 25°–37°C, and the volume quantities of the reaction are conveniently 1–10 ml. The enzymatic activity measured is indicated in standard international units (U), one enzyme unit (IU) being defined as that amount of enzyme which converts $10^{-6}$ mole of substrate (e.g., N-benzoyl-L-arginine ethyl ester) per minute.

In addition to this activity determination on a low-molecular weight substrate, it is similarly possible to effect a measurement of enzyme activity on high-molecular substrates in a conventional manner. For example, hemoglobin is frequently used as a proteolytic substrate in order to measure proteolytic activity, e.g., in accordance with Northrup's methods indicated in the literature.

Because of their many advantageous properties, biologically active compounds affixed in accordance with this invention can be utilized in a wide variety of ways. They are highly suitable for reactions in column packings, since they have good mechanical properties and high transit speeds can be obtained. For example, low-molecular weight substances fixed according to this invention and packed in the form of a column provide a great advantage in enzyme purification with the aid of affinity chromatography and/or biospecific adsorption. For instance, by passing an enzyme mixture in a solution of moderate ionic strength over such a column containing an immobilized enzyme effector, the enzyme which has an affinity for the insoluble effector is selectively adsorbed. By varying the elution conditions, e.g., ionic strength and pH, or by the addition of excess effector to the elution buffer, the enzyme can then again be desorbed in a conventional manner.

Of course, it is also possible to advantageously employ the immobilized enzymes according to this invention as column packings. The substrate-containing reaction mixture is then passed through this column, where it comes into contact with the enzymatic catalyst, and the reaction products leave the column free of enzyme impurities. The column packing can be used for a rather long period of time in this way, e.g., 30 days at 25°C in the case of immobilized papain.

The use of immobilized enzymes and particularly of enzymes which have been rendered insoluble has gained increasing importance in industrial processes, e.g., in the fermentation industry, in the production of antibiotics, and in chemical and/or biological syntheses. Additional fields of application include but are not limited to metabolic investigations, especially for diagnostic purposes, and the use as medicines, specifically upon topical, but also with oral and parenteral administration, where the fixed enzymes are preferably administered in the form of microcapsules.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth in degrees Celsius; unless otherwise indicated, all parts and percentages are by weight.

In the following Examples, the CMC hydrazides were prepared from CMC having an average degree of polymerization of about 1500 glucose units per molecule corresponding to a molecular weight of about 25000.

The acrylic acidhydrazide-acrylamide copolymers had a molecular weight of about 10000 – 30000 and a mole ratio of acid-hydrazide:amide of about 1:5.

EXAMPLE 1

2 g. of CMC hydrazide (with 3.2 meq./g. acid hydrazide groups) is dissolved in 100 ml. of water. The solution is adjusted to pH 4.5 with HCl and combined with 0.6 ml. of a 25% aqueous solution of glutaric dialdehyde. The mixture immediately assumes a high viscosity, and after 2-3 minutes, a gel-like polymer is precipitated. A homogeneous suspension is produced by agitation, cooled to 0°–2°, and the pH is lowered by adding 5N HCl to a value of 1.2. 10.4 ml. of a 5% aqueous $NaNO_2$ solution is then added to the reaction mixture. After 15 minutes, the polymer, which contains acid azide groups, is filtered, washed with water, and immediately made into a homogeneous suspension with 1 g. of crystalline trypsin dissolved in 100 ml. of 0.2 M triethanolamine/HCl buffer (2 mM $CaCl_2$; pH 8.5), which solution was precooled to 2°. After 2 hours, the protein which has not been bound in a covalent linkage is removed by repeated washing with 0.3 M phosphate buffer (pH 8.0), as well as 1 M NaCl solution. Matrix-bound trypsin is thus obtained having the schematic partial formula R—O—$CH_2$CONH—trypsin (R = partially cross-linked cellulose strand). Of the provided enzyme, 52% is bound to the matrix by a covalent linkage. The thus-bound trypsin is still enzymatically active to an extent of 80-90% against N-benzoyl-arginine ethyl ester — HCl (BAEE).

EXAMPLE 2

In accordance with Example 1, 2 g. of CMC hydrazide is cross-linked with glutaric dialdehyde and reacted with 2.8 g. of p-nitrobenzaldehyde in 40 ml. of acetic acid for 1 hour at 25°. Then the thus-formed polymeric hydrazone is filtered, washed thoroughly with methanol and water, and suspended in 400 ml. of water. After rendering the reaction mixture alkaline with dilute ammonia (pH about 10-11), the nitro groups are reduced with 10 g. of $Na_2S_2O_4$ for 2 hours at 25°. The thus-formed amine is filtered, washed with water and methanol, and suspended in 400 ml. of 0.1N HCl, precooled to 5°. For diazotization purposes, 5 ml. of 5% $NaNO_2$ solution is added dropwise to the reaction mixture. The latter is allowed to react for 30 minutes; then the polymer containing diazonium groups is filtered and washed repeatedly with 0.2 M phosphate buffer (pH 7.8). The moist filter cake is subsequently suspended homogeneously immediately in 150 ml. of a precooled solution of 500 mg. of papain and reacted for 18 hours under ice cooling. Thereafter, the protein which has not formed a covalent linkage is washed out as described in Example 1. The product is matrix-bound papain having the partial formula

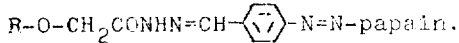

Of the enzyme employed, 66% is in covalent linkage with the matrix. The thus-bound papain has an enzymatic activity of 90% against BAEE as the substrate.

EXAMPLE 3

In accordance with Example 1, 2 g. of CMC hydrazide is cross-linked with glutaric dialdehyde. After reaction with $NaNO_2$, the polymer which contains acid azide groups is homogeneously suspended in a solution, cooled to 5°, of 4 g. of hexamethylenediamine in 100 ml. of water. After 2 hours, the pH is lowered to 4, the polymer, which contains amino groups, is filtered, washed, and suspended in 100 ml. of 0.2 M triethanolamine/HCl buffer (pH 8.5). Under agitation, 100 ml. of a 2.5% aqueous solution of glutaric dialdehyde is added thereto, and the mixture is allowed to react for 2 hours at room temperature. Thereafter, the "activated" polymer containing aldehyde groups is filtered, washed, and homogeneously suspended in 200 ml. of a solution, cooled to 5°, of 1 g. of crystalline trypsin in 0.2 M triethanolamine/HCl buffer (2 mM $CaCl_2$; pH 8.5). After 18 hours, the protein which has not formed a covalent linkage is washed out as set forth in Example 1, thus obtaining matrix-bound trypsin of the partial formula R—O—$CH_2$CONH$(CH_2)_6$N=CH$(CH_2)_3$CH=N—trypsin. Of the enzyme employed, 26% is bound by covalent linkage to the polymeric matrix. The thus-bound trypsin is enzymatically active to an extent of 90-100%, measured against BAEE as the substrate.

EXAMPLE 4

In accordance with Example 3, 2 g. of CMC hydrazide is converted into the "activated" polymer containing aldehyde groups and homogeneously suspended in 200 ml. of a solution, precooled to 5°, of 0.6 g. of crystalline α-chymotrypsin in 0.2 M triethanolamine/HCl buffer (2 mM $CaCl_2$; pH 8.5). After 18 hours, the protein which has not formed a covalent linkage is washed out as described in Example 1, thus obtaining matrix-bound α-chymotrypsin of the partial formula R—O—$CH_2$CONH$(CH_2)_6$N=CH$(CH_2)_3$CH=N—α-chymotrypsin. 80% of the enzyme employed is bound by covalent linkage to the matrix. The thus-bound α-chymotrypsin has an enzymatic activity against N-glutaryl-L-phenylalanine-4-nitroanilide as the substrate of 90-100%.

EXAMPLE 5

According to Example 3, 2 g. of CMC hydrazide is converted into the "activated" polymer containing aldehyde groups and homogeneously suspended in 150 ml. of a solution, precooled to 5°, of 0.6 g. of crystalline ribonuclease (from bovine pancreas) in 0.2 M phosphate buffer (pH 7.8). After 18 hours, the protein which is not bound in a covalent linkage is washed out as set forth in Example 1, thus producing matrix-bound ribonuclease of the partial formula R—O—$CH_2$CONH$(CH_2)_6$N=CH$(CH_2)_3$CH=N-ribonuclease. Of the enzyme utilized, 28% forms a covalent bond with the matrix. The thus-bound ribonuclease is enzymatically active to an extent of 76% against cytidine-2',3'-cyclophosphate as the substrate.

EXAMPLE 6

2 g. of CMC hydrazide is dissolved in 200 ml. of water and adjusted to pH 4.5 with a few drops of HCl. Under agitation, 50 ml. of 5% aqueous glutaric dialdehyde solution is added thereto. A water-insoluble gel is formed at once. After 2 hours at 25°, the polymer containing aldehyde groups is filtered and freed of excess aldehyde by thorough washing with water. The washed-out filter cake is immediately made into a homogeneous suspension with a solution, precooled to 5°, of 400 mg. of crystalline ribonuclease in 200 ml. of 0.2 M phosphate buffer (pH 8.0). After 18 hours, the protein which has not formed a covalent linkage is washed out as indicated in Example 1. 28% of the enzyme employed is bound in a covalent linkage to the matrix. The thus-bound ribonuclease has an enzymatic activity of 82% against cytidine-2',3'-cyclophosphate as the substrate. The matrix-bound enzyme produced in this way (about 30 g. of moist material) is homogeneously suspended in 250 ml. of 0.1 M NaBH₄ solution in order to eliminate unreacted aldehyde groups and reduced for 20 minutes at 0°. Then, 2N HCl is added to a pH of 4.0, and the matrix-bound enzyme of the partial formula R—O—CH₂CONH—NH—(CH₂)₅—NH-ribonuclease is well washed with water and 0.1 M phosphate buffer (pH 7.8). The thus-bound ribonuclease is still enzymatically active to an extent of 70%.

EXAMPLE 7

In accordance with Example 6, the "activated" polymer containing aldehyde groups is produced from 2 g. of CMC hydrazide and homogeneously suspended in a solution of 500 mg. of crystallized trypsin in 200 ml. of 0.2 M triethanolamine/HCl buffer (2 mM CaCl₂; pH 8.5) at 5°. After 18 hours, the protein which is not bound by covalent linkage is washed out as set forth in Example 1. Of the enzyme employed, 30% is bound by covalent linkage to the matrix. The thus-bound trypsin is enzymatically active against benzoyl-L-arginine ethyl ester as the substrate to an extent of 90%. After treatment with NaBH₄ analogously to Example 6, matrix-bound trypsin is obtained of the partial formula R—O—CH₂CONH—NH—(CH₂)₅—NH-trypsin, the activity of which is still 86%.

EXAMPLE 8

2 g. of a water-soluble copolymer of acrylic acid hydrazide and acrylamide (2.7 meq./g. acid hydrazide groups) is suspended in 100 ml. of 0.2 M triethanolamine/HCl buffer (pH 8.0) and reacted for 3 hours with 100 ml. of 5% aqueous glutaric dialdehyde solution at 25°. The excess dialdehyde is washed out with water, and the activated copolymer is immediately homogeneously suspended in a solution, precooled to 5°, of 1 g. of crystallized trypsin in 160 ml. of 0.2 M triethanolamine/HCl buffer (0.01 M CaCl₂; pH 8.5). After 18 hours, the protein which has not formed a covalent linkage is washed out as described in Example 1, thus obtaining matrix-bound trypsin of the partial formula R—CONHN=CH(CH₂)₃CH=N—trypsin (R = partially cross-linked —CH—CH₂—strand).
  |

Of the enzyme employed, 10% forms a covalent linkage with the matrix. The bound trypsin has an enzymatic activity of 80% against BAEE.

EXAMPLE 9

10 g. of CMC hydrazide is suspended in 200 ml. of dimethylformamide (DMF). The suspension is mixed with 105 ml. of 25% glutaric dialdehyde solution and agitated for 18 hours at 25°. Thereafter, the activated carrier is filtered, washed with DMF, again suspended in 100 ml. of DMF, and mixed with a solution of 17.6 g. of p-aminophenylmercuric acetate in 150 ml. of DMF. The mixture is stirred for 4 hours at 25°. Thereafter, the charged matrix is filtered, washed with DMF and with methanol, and dried at 40°, thus obtaining 11.2 g. of matrix-bound p-aminophenylmercuric acetate of the partial formula

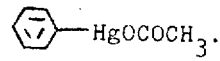

Hg content: 3.2%, corresponding to 0.16 millimole of p-aminophenylmercuric acetate per gram of dry substance.

EXAMPLE 10 a. 100 g. of CMC hydrazide is dissolved at 0°-4° in 5 l. of 0.5N HCl. To this solution is gradually added dropwise 330 ml. of 1.5N NaNO₂ solution. The thus-formed CMC azide is removed by centrifuging and washed several times with cold 0.001N HCl. Then, the CMC azide is suspended in 4 l. of cold 0.3 M hexamethylenediamine solution and stirred overnight under ice cooling. The partially cross-linked reaction product is removed by centrifuging, and washed several times with water, dilute hydrochloric acid (pH 4), dilute NaOH (pH 8), and finally again with water. The thus-obtained N-(6-aminohexyl)-carbamoylmethylcellulose ("aminoalkyl-(C₆)-cellulose," AAC) is lyophilized. The yield is 70 g. and the content of NH₂ groups is 115 meq./g. of dry substance.

Analogously, the reaction of CMC azide with octamethylenediamine and dodecamethylenediamine yields partially cross-linked aminoalkyl-(C₈)- and aminoalkyl-(C₁₂)-cellulose.

b. 5 g. of partially cross-linked AAC is suspended in 500 ml. of 0.1 M triethanolamine buffer (tram buffer, pH 8.5) and combined, for purposes of activation, with 38 ml. of 25% glutaric dialdehyde solution. The mixture is agitated overnight at 25°, filtered, and the activated matrix is washed with 0.1 M tram buffer. Then, the activated matrix is suspended in 500 ml. of a 0.04 M alanine-p-nitranilide (alpha) solution in 0.1 M tram buffer. The suspension is stirred for 2 hours at 25°, filtered, and the polymer-bound alapa is washed until the rinse water no longer assumes a yellow color upon the addition of sodium hydroxide solution. The thus-obtained polymer-bound alapa, having the partial formula

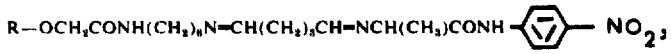

is freeze-dried. Yield: 4.6 g. Concentration: 0.42 millimole of alapa per gram of dry substance.

EXAMPLE 11

100 g. of partially cross-linked AAC (about 100 meq. NH₂ groups) is suspended at 0°-4° in 1.5 l. of 0.1 M phosphate buffer (pH 8) and combined with 200 g. of succinic anhydride. During the reaction, the pH is maintained at 7.8-8.2 by adding NaOH. The mixture is agitated overnight, then filtered and washed with NaH- CO₃ solution, water, phosphate buffer (pH 5.5), and again with water. The thus-formed succinylated aminoalkylcellulose (SAAC) is lyophilized. Yield: 104.3 g. COOH groups: 0.89 meq./g.

5 g. of SAAC is suspended in 500 ml. of a 0.04 M alapa solution in 0.1 M phosphate buffer (pH 5). Within 5 minutes, 80 ml. of a 0.1 M solution of N-cyclohexyl-N'-[2-(N-methylmorpholinium)-ethyl]-carbodiimide p-toluenesulfonate (CDI) is added dropwise thereto. The mixture is agitated thereafter overnight at 25° and a pH of 4.7 – 5.

Then, the reaction product of the schematic formula

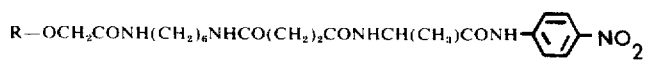

is filtered, and washed with 0.05 M Na-ethylenediaminetetraacetate (EDTA) solution (pH 7) and with water. The reaction product is lyophilized. Yield: 6.3 g. Fixed material: 0.89 millimole alapa/g. dry substance.

EXAMPLE 12

30 g. of SAAC is suspended in 1 l. of a solution of 30 g. of pyridoxamine phosphate (PAMP) in 0.1 M phosphate buffer (pH 5). Under agitation, 250 ml. of a 0.2 M CDI solution is added dropwise thereto within 5–10 minutes. The mixture is then stirred overnight at 25° and a pH of 4.7 – 5. The polymer-bound PAMP is filtered and washed with phosphate buffer (pH 5.5), water, NaHCO₃ solution, water, NaCl solution, and again with water. The product is stored in the moist state. Yield: 212 g. of moist matrix-bound pyridoxamine phosphate. For purposes of analysis, 2 g. of the moist material is dried under reduced pressure at 40°, thus obtaining 0.32 g. of dry substance. The dry substance has a nitrogen content of 3.8% and a phosphorus content of 0.95%, corresponding to 0.29 millimole of PAMP per gram of dry substance.

EXAMPLE 13

The procedure of Example 12 is followed, except for the use of 0.1 mole (= 13.7 g.) of m-aminophenylboronic acid as the substrate, thus obtaining 33.4 g. of dry matrix-bound m-aminophenylboronic acid. Boron content: 0.45%, corresponding to 0.41 millimole/g. dry substance.

EXAMPLE 14

10 g. of SAAC is suspended in 120 ml. of 0.1 M CDI solution in 0.1 M 2-morpholinoethanesulfonic acid buffer (pH 5) and agitated for 30 minutes at 25°. Thereafter, 4 g. of p-aminobenzamidine dihydrochloride is added thereto, and the mixture is stirred for 1.5 hours at a pH of 4.7 – 5. Then, 5 g. of solid CDI is once more added thereto, and the mixture is agitated for another 3 hours. The reaction product is washed with buffer solution, 1 M NaCl solution, 0.05 M EDTA solution (pH 7.3), and water, and lyophilized. Yield: 9.8 g. of matrix-bound p-aminobenzamidine. Nitrogen increase: 2%, corresponding to 0.475 millimole of p-aminobenzamiidine/g. dry substance.

EXAMPLE 15

10 g. of SAAC is suspended in a solution of 5.3 g. of p-aminophenylmercuric acetate in 200 ml. of DMF. The suspension is adjusted to pH 5 with dilute HCl. Then, 200 ml. of 0.08 M CDI solution is added thereto, the pH being maintained at 4.7 – 5. The mixture is stirred for 1 hour, then another 100 ml. of CDI solution is added dropwise, and the stirring is continued overnight. Thereafter, the thus-obtained matrix-bound p-aminophenylmercuric acetate is filtered, washed with DMF, DMF/water (1:1), and water, and lyophilized. Yield: 11 g. Hg content: 5.35% corresponding to 0.265 millimole/g. of dry substance.

EXAMPLE 16

26 g. of SAAC is suspended in 400 ml. of a 0.15 M L-lysine-p-nitranilide solution in 0.1 M phosphate buffer (pH 5). While controlling the pH, 250 ml. of 0.15 M CDI solution (in water) is added thereto, and the mixture is agitated for 1 hour while controlling the pH, and furthermore overnight.

The polymer-bound L-lysine-p-nitranilide is filtered, washed twice with 1 M NaCl solution and once with water, then suspended in 1 N NaOH in order to split off p-nitroaniline, and incubated at 60° for 30 minutes. The polymer-bound L-lysine is washed with 1 M NaCl solution, 0.2 M Na₂HPO₄ solution (pH 9), 0.2 M NaH₂PO₄ solution (pH 4.5), 0.05 M EDTA solution (pH 7), 1 M NaCl solution, and water, and then lyophilized. Yield: 15.2 g. Affixed substance: 0.7 millimole of L-lysine per gram of dry substance (calculated from the amount of the split-off p-nitroaniline).

EXAMPLE 17

10 g. of SAAC is suspended in 300 ml. of a solution of 6.75 g. of estrone in DMF, and the pH is adjusted to 5.5. Then, 50 ml. of aqueous 0.2 M CDI solution is added under pH control, and the mixture is stirred for 1 hour. Thereafter, another 50 ml. of CDI solution is added and the mixture agitated for another 3 hours. The thus-obtained matrix-bound estrone is filtered, washed with DMF and water, and lyophilized. Yield: 10.8 g. Affixed material: 0.167 millimole of estrone per gram of dry substance.

EXAMPLE 18 a. 100 g. of CMC hydrazide is partially cross-linked with glutaric dialdehyde, as described in Example 1, then diazotized, and washed with cold 0.001 M HCl. The thus-produced azide is stirred into 1.5 l. of cold 1 M 6-aminocaproic acid (pH 5.5) and homogenized. The mixture is stirred for 1 hour under ice cooling and pH control, and then is agitated overnight at 5°.

The thus-obtained "carboxyalkylcellulose" of the schematic formula R—O—CH₂—CO—NH—(CH₂-)₆—COOH is filtered off, washed with water, NaHCO₃ solution, EDTA solution, and again with water, and lyophilized. Yield: 69 g. Content of COOH groups: 0.445 meq/g dry substance.

b. 10 g of the thus-produced "carboxyalkylcellulose" is suspended in 300 ml. of a solution of 6.8 g. of estradiol in DMF. Then, 30 ml. of aqueous 0.2 M CDI solution is added thereto, and the procedure of Example 17 is then followed, wherein also during the second addition of carbodiimide, only 30 ml. is added. Yield: 10.45 g. Affixed substance: 98 millimole of estradiol per gram of dry substance.

EXAMPLE 19

10 g. of a water-soluble copolymer of acrylic acid hydrazide and acrylamide with 2.7 meq. acid hydrazide groups/g. is diazotized analogously to Example 10(a) with $HNO_2$ and thereafter immediately reacted with 500 ml. of 0.5 M tetramethylenediamine solution. After washing out with water, the partially crosslinked copolymer of acrylamide and N-(4-aminobutyl)-acrylamide is "activated" analogously to Example 10(b) with glutaric dialdehyde, and reacted with alapa. After freeze-drying, 8.2 g of a product is obtained having the schematic formula

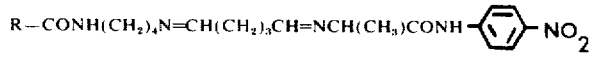

(R=partially crosslinked $CH-CH_2$ strand), containing 0.55 millimole of alapa per gram of dry substance.

EXAMPLE 20

10 g. of CMC hydrazide is dissolved in 500 ml. of 0.001N NaOH, mixed with 4 g. of 1,3-bis(2,3-epoxy-propoxy)butane, and maintained at 50° for 2 hours. The partially cross-linked CMC hydrazide is washed out with water, "activated" with glutaric dialdehyde analogously to Example 9, and reacted with p-aminophenylmercuric benzoate, thus obtaining 9.5 g. of a reaction product containing 0.2 millimole of p-aminophenylmercuric benzoate per g. of dry substance.

EXAMPLE 21

2 g. of CMC hydrazide is dissolved in 100 ml. of 0.1N NaOH, mixed with 0.3 g. of epichlorohydrin, and maintained at 50° for 2 hours. The partially cross-linked CMC hydrazide is washed with water. Analogously to Example 1, the free acid hydrazide groups are diazotized with $HNO_2$ and reacted with trypsin. 40% of the enzyme are affixed to the matrix. The thus-bound trypsin still has an enzymatic activity of 85% against BAEE.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A water-insoluble, partially covalently cross-linked carboxymethylcellulose hydrazide derivative having a swelling capacity, measured as water absorption per gram of dry material, of 10–80 ml. $H_2O$/g., an average of about 150–2,000 glucose units per molecule and containing about 2–4.5 meq. of acid hydrazide groups per gram of dry material, wherein at least 10% of said hydrazide groups are cross-linked by —CO—NH—Z—Y—Z'—NH—CO— groups wherein Y is a single covalent bond or a linear divalent alkylene chain of 1–18 carbon atoms interrupted by 0–4 oxygen atoms, Z and Z' are each a single covalent bond, —N = CH—, —$NHCH_2$—, —$NHCH_2CHOH$—, —NHCO—, —NH—CO—NH— or —NH—CS—NH—.

2. A carboxymethylcellulose derivative according to claim 1, wherein Z and Z' are alike.

3. A carboxymethylcellulose derivative according to claim 2, wherein at least 70% of the hydrazide groups are uncross-linked.

4. A carboxymethylcellulose derivative according to claim 3, wherein 15–20% of the hydrazide groups are cross-linked.

5. A carboxymethylcellulose derivative according to claim 4, containing about 1,500 glucose units per molecule.

6. A carboxymethylcellulose derivative according to claim 1, wherein Y is divalent alkylene of 1–8 carbon atoms interrupted by 0–4 oxygen atoms.

7. A carboxymethylcellulose derivative according to claim 6, wherein Y is divalent alkylene of 3–6 carbon atoms.

8. A carboxymethylcellulose derivative according to claim 1, which is cross-linked by glutaric dialdehyde.

9. A carboxymethylcellulose derivative according to claim 1, which is cross-linked by 1,3-bis(2,3-epoxy-propoxy)butane.

10. A carboxymethylcellulose derivative according to claim 1, which is cross-linked by epichlorohydrin.

11. A carboxymethylcellulose derivative according to claim 1, which is cross-linked by conversion of said hydrazide groups to azide groups and cross-linking of the resultant azide groups with an alkylenediamine to form an N-(6-aminoalkyl)-carbamoyl methylcellulose.

12. A carboxymethylcellulose derivative according to claim 1, wherein uncross-linked acid hydrazide groups are substituted by reactive groups comprising at least one member selected from the group consisting of azide, —CHO, —$CH_2Cl$, —$CH_2Br$, —$CH_2I$,

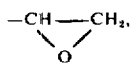

—$NH_2$, —COCl, —COBr, —COI, —NCO, —SCN, —COOH or diazonium salt groups.

13. A carboxymethylcellulose derivative according to claim 12, wherein said reactive groups are acid azide groups.

14. A carboxymethylcellulose derivative according to claim 12, wherein said reactive groups are free aldehyde groups.

15. A carboxymethylcellulose derivative according to claim 12, wherein said reactive groups are carboxyl groups.

16. A carboxymethylcellulose derivative according to claim 12, wherein said reactive groups are diazonium salt groups.

17. A carboxymethylcellulose derivative according to claim 12, which is partially cross-linked by glutaric dialdehyde or hexamethylenediamine.

18. A carboxymethylcellulose derivative according to claim 12, which is cross-linked by conversion of said hydrazide groups to a corresponding azide and cross-linking the resultant azide with an alkylenediamine to form an N-(6-aminoalkyl)-carbamoyl methylcellulose.

19. A carboxymethylcellulose derivative according to claim 18, wherein said N-(6-aminoalkyl)-carbamoyl methylcellulosoe is succinylated aminoalkylcellulose.

20. A biochemically active water-swellable or water-insoluble preparation comprising at least one biochemically active compound covalently bonded to the polymeric material according to claim 12.

21. A preparation according to claim 20, wherein said biochemically active compound is a protein or polypeptide.

22. A preparation according to claim 21, wherein said biochemically active compound is an enzyme or enzyme effector.

23. A preparation according to claim 22, wherein said biochemically active compound is a protease or peptidase.

24. A process for preparing a carboxymethylcellulose derivative according to claim 1, which comprises reacting an uncross-linked, water-soluble carboxymethylcellulose polymer containing cross-linkable acid hydrazide or azide groups with a bifunctional cross-linking agent reactive with said groups to covalently cross-link a portion of said groups and thereby form said derivative.

25. A process according to claim 24, wherein said bifunctional cross-linking agent is glutaric dialdehyde or hexamethylenediamine.

26. A process according to claim 24, further comprising substituting uncross-linked acid hydrazide groups by reactive groups capable of covalent bonding to an amino, hydroxyl, mercapto or phenyl group of a biochemically active compound, which reactive groups comprise at least one member selected from the group consisting of acid azide groups, —CHO, —CH$_2$Hal,

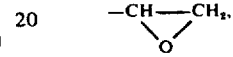

—NH$_2$, —COHal, —NCO, SCN, COOH or diazonium salt groups, in which Hal is Cl, Br or I, to form said derivative.

* * * * *